US010543041B2

United States Patent
Nau, Jr.

(10) Patent No.: US 10,543,041 B2
(45) Date of Patent: *Jan. 28, 2020

(54) ENERGY-BASED SURGICAL INSTRUMENT INCLUDING INTEGRATED NERVE DETECTION SYSTEM

(71) Applicant: COVIDIEN LP, Mansfield, MA (US)

(72) Inventor: William H. Nau, Jr., Longmont, CO (US)

(73) Assignee: Covidien LP, Mansfield, MA (US)

( * ) Notice: Subject to any disclaimer, the term of this patent is extended or adjusted under 35 U.S.C. 154(b) by 125 days.

This patent is subject to a terminal disclaimer.

(21) Appl. No.: 14/862,725

(22) Filed: Sep. 23, 2015

(65) Prior Publication Data

US 2016/0095658 A1 Apr. 7, 2016

Related U.S. Application Data

(60) Provisional application No. 62/059,687, filed on Oct. 3, 2014, provisional application No. 62/059,679, filed on Oct. 3, 2014.

(51) Int. Cl.
*A61B 18/18* (2006.01)
*A61B 5/026* (2006.01)
(Continued)

(52) U.S. Cl.
CPC .......... *A61B 18/1815* (2013.01); *A61B 5/022* (2013.01); *A61B 5/026* (2013.01);
(Continued)

(58) Field of Classification Search
CPC ... A61B 18/22; A61B 5/0084; A61B 5/04001; A61B 5/4893; A61B 5/6848;
(Continued)

(56) References Cited

U.S. PATENT DOCUMENTS 5,409,483 A 4/1995 Campbell et al.
5,833,683 A 11/1998 Fuller et al.
(Continued)

FOREIGN PATENT DOCUMENTS

WO 2012123869 A2 9/2012

OTHER PUBLICATIONS

Fried, "Identification and Imaging of the Nerves Responsible for Erectile Function in Rat Prostate, In Vivo, Using Optical Nerve Stimulation and Optical Coherence Tomography", IEEE Journal of Selected Topics in Quantum Electronics, vol. 13, No. 6, Nov./Dec. 2007, pp. 1641-1645.

*Primary Examiner* — Gary Jackson
*Assistant Examiner* — Zahed Kabir

(57) ABSTRACT

An energy-based surgical system includes a light beam source and a probe defining a channel about a longitudinal axis thereof and a side opening near a distal end thereof. Methods of nerve detection using the system include positioning the probe adjacent targeted tissue, transmitting a beam of light from the light beam source through the channel of the probe and the side opening of the probe to the targeted tissue, measuring a response to determine the presence of a nerve within the targeted tissue, and delivering energy to the targeted tissue with the probe to treat tissue.

12 Claims, 2 Drawing Sheets

(51) Int. Cl.
*A61B 5/022* (2006.01)
*A61B 18/00* (2006.01)

(52) U.S. Cl.
CPC ........... *A61B 2018/00642* (2013.01); *A61B 2018/00904* (2013.01); *A61B 2018/1807* (2013.01); *A61B 2018/1861* (2013.01)

(58) Field of Classification Search
CPC ........... A61B 18/1815; A61B 18/1492; A61B 2018/00023; A61B 2018/00577; A61B 2018/00589; A61B 2018/00601; A61B 2018/0063; A61B 2018/00839; A61B 2018/00994; A61B 2018/1807; A61B 2018/2238
USPC .......................................................... 606/3
See application file for complete search history.

(56) References Cited

U.S. PATENT DOCUMENTS

| | | | |
|---|---|---|---|
| 6,035,229 A * | 3/2000 | Silverstein | A61B 1/00082 600/117 |
| 2003/0097129 A1* | 5/2003 | Davison | A61B 18/14 606/41 |
| 2004/0077934 A1* | 4/2004 | Massad | A61B 5/0205 600/300 |
| 2005/0099824 A1 | 5/2005 | Dowling et al. | |
| 2009/0054908 A1 | 2/2009 | Zand et al. | |
| 2011/0066144 A1* | 3/2011 | Bonn | A61B 18/1815 606/33 |
| 2011/0172659 A1 | 7/2011 | Brannan | |
| 2012/0029496 A1* | 2/2012 | Smith | A61B 18/02 606/21 |
| 2012/0265198 A1* | 10/2012 | Crow | A61B 18/1492 606/41 |
| 2013/0023910 A1 | 1/2013 | Solomon et al. | |
| 2013/0165764 A1* | 6/2013 | Scheuermann | A61B 5/0095 600/407 |
| 2013/0267874 A1* | 10/2013 | Marcotte | A61B 17/320092 601/2 |
| 2013/0338655 A1 | 12/2013 | Sabati et al. | |
| 2014/0005706 A1* | 1/2014 | Gelfand | A61N 7/022 606/169 |
| 2014/0088629 A1* | 3/2014 | Hastings | A61N 7/022 606/169 |
| 2015/0238259 A1* | 8/2015 | Albeck | A61B 18/22 606/3 |
| 2015/0238260 A1 | 8/2015 | Nau, Jr. | |
| 2016/0095662 A1 | 4/2016 | Nau, Jr. | |

* cited by examiner

ENERGY-BASED SURGICAL INSTRUMENT INCLUDING INTEGRATED NERVE DETECTION SYSTEM

CROSS-REFERENCE TO RELATED APPLICATIONS

This application claims the benefit of, and priority to, U.S. Provisional Patent Application Nos. 62/059,687 and 62/059,679, both of which were filed on Oct. 3, 2014. This application is related to U.S. patent application Ser. No. 14/862,660, filed on Sep. 23, 2015. The entire contents of each of the above applications are hereby incorporated herein by reference.

BACKGROUND

1. Technical Field

The present disclosure relates to surgical instruments and, more specifically, to energy-based surgical instruments including integrated nerve detection systems.

2. Discussion of Related Art

Energy-based surgical instruments apply energy, e.g., RF, microwave, light, ultrasonic, optical, thermal, etc., to tissue to treat tissue during a surgical procedure. Such surgical instruments are typically used in conjunction with a surgical generator that produces an electromagnetic wave, typically above 100 kilohertz, for application to tissue. The electromagnetic wave dissipates energy as heat as it travels through tissue. Electromagnetic frequencies above 100 kilohertz are employed to avoid muscle and/or nerve stimulation. Controlling the duration and intensity of energy application can be used for treating tissue in various manners such as, for example, cutting, dissecting, ablating, arresting blood loss, sealing, coagulating, etc.

During the application of energy to tissue, the heating of tissue can cause damage to nerves in close proximity to the tissue being heated. Although electrical nerve stimulation has been used to detect nerves in close proximity to tissue being treated, electrical nerve stimulation is limited by the need for physical contact between the electrode and nerve-containing tissue, while the spatial precision of the stimulation is limited by the size of the electrode. Electrical nerve stimulation may also produce artifacts that may interfere with the measurement.

Optical nerve stimulation is an alternative to electrical nerve stimulation. A general discussion of optical nerve stimulation can be found in Nathaniel M. Fried et al., *Identification and Imaging of Nerves Responsible for Erectile Function in Rat Prostate, In Vivo, Using Optical Nerve Stimulation and Optical Coherence Tomography*, 13 IEEE J. OF SELECTED TOPICS IN QUANTUM ELECTRONICS 1641, 1642 (2007).

SUMMARY

The devices, systems, and methods of the present disclosure provide for non-contact nerve detection, increased spatial precision of locating nerves, and/or reduced artifacts in measurements by other devices, e.g., X-ray, MRI, and CT scanners.

In aspects of the present disclosure, an energy-based surgical system includes a light beam source and a probe. The light beam source is configured to provide a beam of light. The probe defines a channel about a longitudinal axis thereof and a side opening near a distal end thereof. The channel is operatively connected to the light beam source and is configured to transmit the beam of light from the side opening. In aspects, the system includes a fiber optic cable disposed within the channel that is operatively connected to the light beam source to transmit the beam of light through the side opening. The beam of light may be in a range of about 10 nm to about 1 mm.

In aspects of the present disclosure, the system includes an expandable member wherein a portion of the probe is disposed within the expandable member. The expandable member may be transparent to the beam of light.

In aspects of the present disclosure, the system includes an electrical energy source and a feedline operatively connecting the treatment energy source to the probe to deliver treatment energy to the probe. The probe may include a microwave antenna configured to radiate treatment energy to tissue, or may otherwise be configured to apply treatment energy to tissue to treat tissue. In aspects, the treatment energy is electrical energy having a frequency in the range of about 500 MHz to about 2500 MHz. Alternatively, the treatment energy is electrical energy having a frequency in the range of about 500 MHz to about 10 GHz.

In aspects of the present disclosure, an energy-based surgical device includes a probe defining a channel about a longitudinal axis thereof and a side opening near a distal end thereof. The channel is configured to transmit a beam of light from a light beam source through the side opening. The energy-based surgical device may include a fiber optic cable disposed within the channel that is configured to transmit the beam of light from the light beam source through the side opening. The probe may be configured to radiate or otherwise apply treatment energy to tissue to treat tissue.

In aspects of the present disclosure, the energy-based device includes an expandable member and a portion of the probe is disposed within the expandable member. The expandable member may be transparent to the beam of light.

In aspects of the present disclosure, a method of nerve detection includes providing an energy-based system including a light beat source and a probe defining a channel about a longitudinal axis thereof and a side opening near a distal end thereof. The method further includes positioning the probe adjacent targeted tissue, transmitting a beam of light from the light beam source through the channel and the side opening to the targeted tissue, measuring a response to determine the presence of a nerve within the targeted tissue, and delivering energy to the targeted tissue with the probe to treat tissue. The method may include repositioning the probe in response to the presence of a nerve within the targeted tissue before delivering energy to the targeted tissue with the probe. The method may include determining whether a nerve is damaged by delivering a beam of light from the light beam source through the channel and the side opening of the probe to the targeted tissue and measuring a response after delivering energy to the targeted tissue with the probe. In aspects, the energy-based surgical system further includes a fiber optic cable disposed within a channel of the probe such that the beam of light is delivered from the light beam source through the fiber optic cable.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Figure 1:
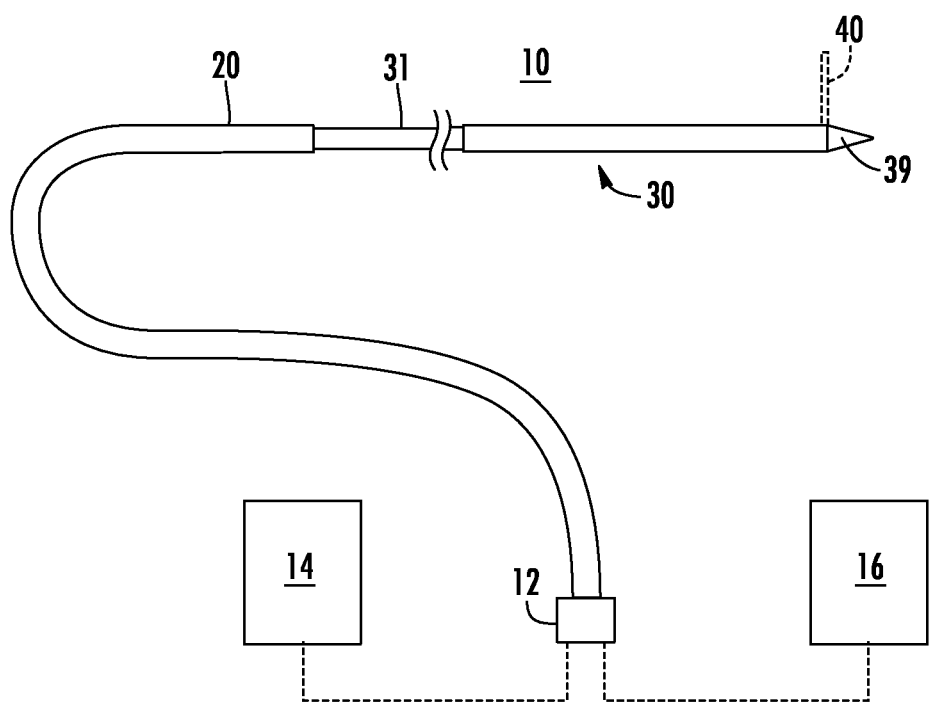
FIG. 1 is a schematic diagram of an energy-based surgical system for treating tissue that includes optical nerve detection, provided in accordance with the present disclosure.

Embodiments of the present disclosure are described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is furthest from the clinician.

In accordance with the present disclosure, various embodiments of devices, systems, and methods for applying energy to tissue to treat a target volume of tissue are provided. These embodiments may be implemented using any suitable form of energy, e.g., RF, microwave, light, ultrasonic, optical, thermal, etc., and for any suitable tissue treatment, e.g., cutting, dissecting, ablating, arresting blood loss, sealing, coagulating, etc. Thus, the present disclosure is equally applicable for use with any energy-based surgical instrumentation and/or for any energy-based tissue treatments.

Figure 2:
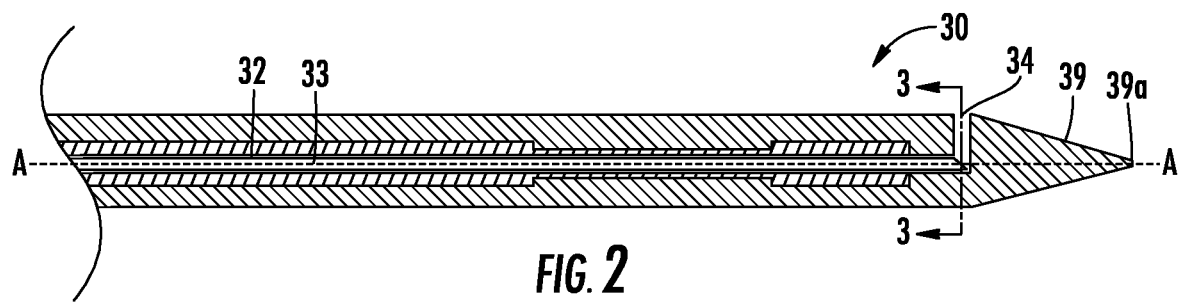
FIG. 2 is a longitudinal cross-sectional view of the probe of the system shown in FIG. 1.

Referring now to FIGS. 1 and 2, an energy-based surgical system with optical nerve detection 10 provided in accordance with the present disclosure is shown including an energy applicator or probe 30. Probe 30 is operably connected by a feedline 31 to a light energy source 14 and a treatment energy source 16, although light energy source 14 and treatment energy source 16 may be combined within a single source, e.g., a multi-function generator. As noted above, the treatment energy source may supply any suitable form of energy including, but not limited to, RF, microwave, light, ultrasonic, optical, thermal, etc. Probe 30 is configured to deliver treatment energy to targeted tissue as well as to deliver light energy to targeted tissue as described in detail below.

Feedline 31 may be formed from a suitable flexible, semi-rigid, or rigid cable and may connect directly to light energy source 14 and/or treatment energy source 16. Alternatively, the feedline 31 may operably connect probe 30 to light energy source 14 and/or treatment energy source 16 via a transmission line 20. As used herein, "transmission line" generally refers to any transmission medium that can be used for the propagation of signals from one point to another.

Feedline 31 may have a variable length from a proximal end of probe 30 to a distal end of transmission line 20 ranging from a length of about one inch to about twelve inches, although other dimensions are also contemplated. Feedline 31 may be formed of suitable electrically conductive materials, e.g., copper, gold, silver, or other conductive metals or metal alloys having similar conductivity values. Feedline 31 may be made of stainless steel, which generally offers the strength required to puncture tissue and/or skin. Conductive materials used to form feedline 31 may be plated with other materials, e.g., other conductive materials, such as gold or silver, to improve their properties, e.g., to improve conductivity, decrease energy loss, etc. In some embodiments, feedline 31 includes stainless steel, and to improve the conductivity thereof, the stainless steel may be coated with a layer of a conductive material such as copper or gold. Feedline 31 may include an inner conductor, a dielectric material coaxially surrounding the inner conductor, and an outer conductor coaxially surrounding the dielectric material. Feedline 31 may be cooled by fluid, e.g., saline, water, or other suitable coolant fluid, to improve power handling, and may include a stainless steel catheter. Other configurations are also contemplated.

Located at the distal end of probe 30 is an end cap or tapered portion 39, which may terminate in a sharp tip 39a to allow for insertion into tissue with minimal resistance. Tapered portion 39 may include other shapes, such as, for example, a tip 39a that is rounded, flat, square, hexagonal, or cylindroconical.

With continued reference to FIGS. 1 and 2, light energy source 14 is configured to produce a beam of light 40 having a wavelength in a range of about 10 nm (ultraviolet) to about 1 mm (infrared), although other suitable wavelengths are also contemplated, and deliver the beam of light 40 to probe 30 via feedline 31. Probe 30, in turn, delivers beam of light 40 to targeted tissue. Probe 30 defines a channel 32 about a longitudinal axis "A-A" thereof. Channel 32 extends through feedline 31 and substantially through probe 30 to a point adjacent tapered portion 39, although channel 32 may alternatively be positioned alongside or in any other suitable relation relative to longitudinal axis "A-A" and/or may extend at least partially into tapered portion 39 of probe 30. Channel 32 includes, at its distal end, a radial, or side opening 34 adjacent to tapered portion 39. Side opening 34 may extend perpendicularly relative to longitudinal axis "A-A" or at any other suitable angle relative thereto. A fiber optical cable 33 is disposed within channel 32 to deliver beam of light 40 from light energy source 14 to tissue as described in detail below. Fiber optic cable 33 extends through transmission line 20 to a connector 12. The distal end of the fiber optic cable 33 is angled to direct the beam of light 40 through the side opening 34. Additionally or alternatively, the distal end of the fiber optic cable 33 may be associated with a refractive or reflective element to direct the beam of light 40 through the side opening 34. Connector 12 operatively connects light energy source 14 and/or treatment energy source 16 to feedline 31.

Figure 3:
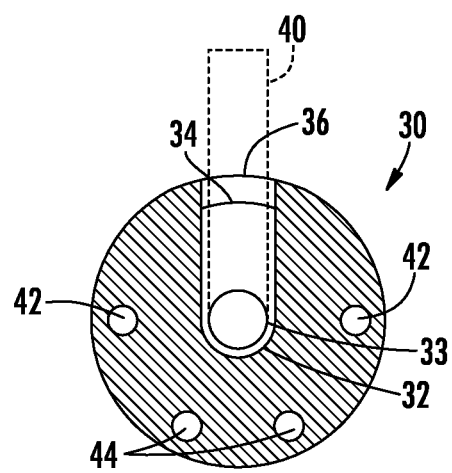
FIG. 3 is a cross-sectional view taken along section line "3-3" of FIG. 2.

Referring additionally to FIG. 3, probe 30 may include a window 36 positioned over side opening 34 to sealingly enclose the distal end of channel of 32. In embodiments, probe 30 includes cooling conduits 44. Cooling conduits 44 may form a closed circuit with a source of cooling fluid (not shown). The source of cooling fluid may be within treatment energy source 16 or be provided as a separate unit. Examples of cooling systems incorporating such cooling conduits are detailed in commonly assigned U.S. Pat. Nos. 7,311,703 and 8,118,808, the contents of each of which are hereby incorporated in its entirety.

During a surgical procedure, probe 30 is inserted into or placed adjacent to targeted tissue to be treated. Beam of light 40 is generated by light beam source 14 and delivered to probe 30 through feedline 31 and, ultimately, to the targeted tissue through fiber optic cable 33 and side opening 34 of probe 30 to detect the presence of nerves in the targeted tissue. The detection of nerves may be performed before, after, or during the delivery of energy to the targeted tissue.

As noted above, beam of light 40 is delivered to the targeted tissue through fiber optic cable 33, which is disposed within channel 32 of probe 30. Beam of light 40 may be delivered in a "top hat" beam profile to minimize the heating of the targeted tissue. Beam of light 40 may be operated in a "pulse mode" to minimize the heating of the targeted tissue. Alternatively, beam of light 40 may be delivered in a "continuous wave mode" to thermally stimulate a nerve. In the "continuous wave mode," the nerve may be stimulated at temperatures below 45° C.

A response, or lack thereof, is measured as beam of light 40 is delivered to the targeted tissue to determine the presence of a nerve in the targeted tissue. In embodiments, the measured response (or response sought) is a change in blood pressure of the patient, which may result from nerve stimulation via the beam of light 40. The change in blood pressure may be measured as peristalsis along the urethra, e.g., when the targeted tissue is located adjacent the renal nerve. The change in blood pressure may be measured by a pressure cuff over an artery. A blood pressure change of sufficient magnitude may indicate the presence of a nerve in the targeted tissue.

In some embodiments, an electrical sensor is used to measure an electrical response from a nerve present in the targeted tissue. In particular embodiments, the response is measurable by sensing an artificial fibrillation by an electrocardiogram, e.g., when the targeted tissue is cardiac tissue.

It is also contemplated that the response may be measured as a change in blood velocity, the release of hormones, or any other suitable method capable of detecting or measuring a response resulting from nerve stimulation via the beam of light 40.

In use, probe 30 may be used to locate or map nerves within the targeted tissue before a surgical procedure is performed. When a nerve is detected within the targeted tissue before energy is delivered to the targeted tissue, probe 30 may be repositioned and/or the delivery of energy adjusted to minimize the potential damage to the detected nerve. Probe 30 may additionally or alternatively be used to test nerve function before, during, and after a surgical procedure to determine if the nerve has been damaged during the surgical procedure.

Figure 4:
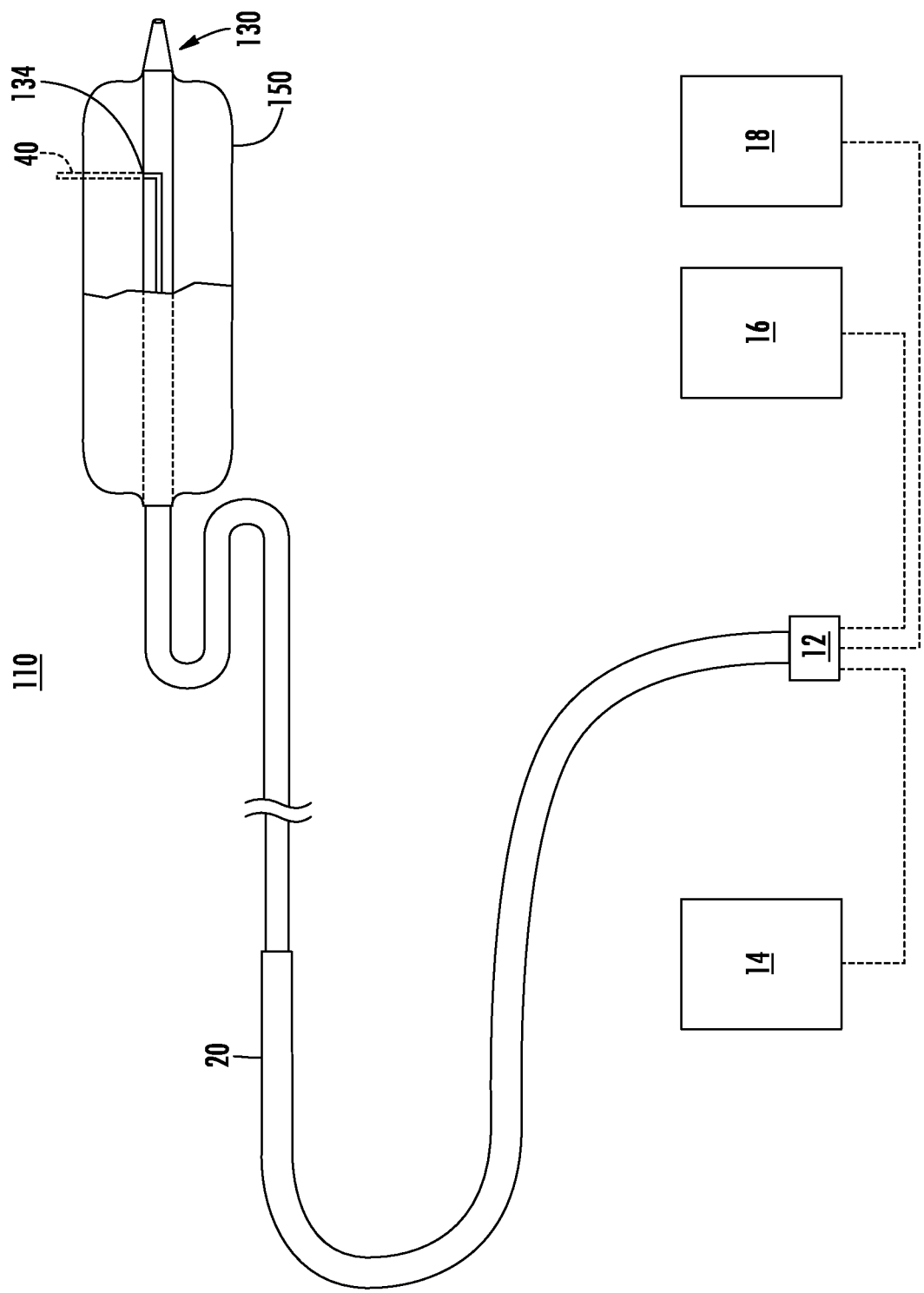
FIG. 4 is a schematic diagram of another energy-based surgical system for treating tissue that includes optical nerve detection, provided in accordance with the present disclosure.

Referring to FIG. 4, another energy-based surgical system having a nerve detection system 110 is provided in accordance with the present disclosure including a probe 130 and an expandable member 150. Probe 130 of system 110 is substantially similar to probe 30 of system 10, for reasons of brevity only the differences will be detailed below.

A portion of probe 130 is disposed within expandable member 150. Expandable member 150 is a fluid expandable member, i.e., a balloon, that engages tissue surrounding probe 130 in response to the injection of an inflation fluid from an inflation source 18. The inflation fluid may be air, water, saline, or any other suitable fluid. Expandable member 150 is used to maintain probe 130 in a fixed position relative to the targeted tissue. Probe 30 may be moveable within expandable member 150 when expandable member 150 is inflated. In embodiments, expandable member 150 is a balloon retractor. In some embodiments, expandable member 150 is a balloon dissector.

As shown in FIG. 4, side opening 134 is positioned within expandable member 150. In such embodiments, the surface of expandable member 150 and the inflation fluid are substantially transparent to beam of light 40. It is also contemplated that side opening 134 may be positioned outside of expandable member 150, i.e., positioned distal to the distal end of expandable member 150.

Referring generally to FIGS. 1-4, in some embodiments, the treatment energy source 16 is configured to provide microwave energy. The microwave energy may be provided at an operational frequency from about 500 MHz to about 2500 MHz. In other embodiments, microwave energy source 16 is configured to provide microwave energy at an operational frequency from about 500 MHz to about 10 GHz.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the claimed invention. Therefore, the above description should not be construed as limiting, but merely as exemplifications of particular embodiments. Those skilled in the art will envision other modifications within the scope and spirit of the claims appended hereto.

What is claimed:

1. A method of nerve detection during a surgical procedure, the method comprising:
   providing an energy-based surgical system including:
      a light beam source;
      a treatment energy source;
      a probe defining a side opening near a distal end thereof;
      a feedline operably coupled to the treatment energy source, extending into the probe, and defining a channel about a longitudinal axis thereof that extends through at least a portion of the probe; and
      a fiber optic cable disposed within the feedline and extending through at least a portion of the channel, the fiber optic cable operably coupled to the light beam source;
   positioning the probe of the energy-based surgical system adjacent targeted tissue;
   transmitting a beam of light from the light beam source through the fiber optic cable and the side opening of the probe to the targeted tissue;
   measuring a physiological response in response to a nerve being stimulated with the beam of light to determine the presence of the nerve within the targeted tissue; and
   delivering treatment energy from the treatment energy source to the targeted tissue, via the feedline and the probe, to treat the targeted tissue, the treatment energy being at least one of RF energy or microwave energy.

2. The method of claim 1, further including repositioning the probe in response to determining the presence of a nerve within the targeted tissue before delivering the treatment energy to the targeted tissue.

3. The method of claim 1, further including, after delivering the treatment energy to the targeted tissue:
   delivering a post-treatment beam of light from the light beam source through the fiber optic cable and the side opening of the probe to the targeted tissue;
   measuring a post-treatment physiological response in response to the nerve being stimulated with the post-treatment beam of light; and
   comparing the post-treatment physiological response to the physiological response to determine whether the nerve has been damaged.

4. The method of claim 1, wherein measuring the physiological response includes detecting a change in blood pressure.

5. The method of claim 4, wherein detecting the change in blood pressure includes measuring blood pressure using a pressure cuff.

6. The method of claim 1, wherein measuring a response includes detecting a change in blood velocity.

7. The method of claim 1, wherein measuring a response includes detecting a release of hormones.

8. The method of claim 1, wherein measuring the response includes detecting a response with an electrical sensor.

9. The method of claim 8, wherein detecting the response with an electrical sensor includes sensing an artificial fibrillation.

10. The method of claim 9, further including displaying the response detected by the electrical sensor.

11. The method of claim 1, wherein delivering the treatment energy to the targeted tissue includes radiating energy from a microwave antenna of the probe.

12. The method of claim 1, wherein delivering the treatment energy to the targeted tissue includes radiating electrosurgical energy from a radio-frequency (RF) antenna of the probe.

* * * * *